US00PP36211P3

(12) United States Plant Patent
Wagner et al.

(10) Patent No.: US PP36,211 P3
(45) Date of Patent: Oct. 22, 2024

(54) ***VACCINIUM* PLANT NAMED 'FC10-076'**

(50) Latin Name: *Vaccinium corymbosum*
Varietal Denomination: FC10-076

(71) Applicant: The Conard Pyle Company, West Grove, PA (US)

(72) Inventors: Adam Wagner, Eugene, OR (US); Peter Stefan Boches, Hilo, HI (US)

(73) Assignee: THE CONARD PYLE COMPANY, West Grove, PA (US)

( * ) Notice: Subject to any disclaimer, the term of this patent is extended or adjusted under 35 U.S.C. 154(b) by 0 days.

(21) Appl. No.: 18/103,778

(22) Filed: Jan. 31, 2023

(65) Prior Publication Data

US 2024/0260493 P1 Aug. 1, 2024

(51) Int. Cl.
*A01H 5/08* (2018.01)
*A01H 6/36* (2018.01)

(52) U.S. Cl.
USPC ..... Plt./157
CPC ..... *A01H 6/368* (2018.05)

(58) Field of Classification Search
USPC ..... Plt./157
CPC . A01H 5/08; A01H 5/00; A01H 6/368; A01H 6/36
See application file for complete search history.

(56) References Cited

U.S. PATENT DOCUMENTS

PP23,336 P2 1/2013 Brazelton et al.

*Primary Examiner* — June Hwu
(74) *Attorney, Agent, or Firm* — Panitch Schwarze Belisario & Nadel LLP; Stephany G. Small; Travis W. Bliss

(57) ABSTRACT

The new *Vaccinium* plant variety 'FC10-076' is provided. 'FC10-076' is a commercial variety. The variety is produced from a cross of 'ZF07-114' (female parent, unpatented) and 'ZF05-032' (male parent, unpatented). The new variety produces white colored inflorescences with calyx ranging from pink to blue in color. A multicolored foliage, including colors of green, pink, and silvery blue is displayed. A moderately vigorous, compact growth habit is exhibited.

2 Drawing Sheets

Latin name of the genus and species: Genus—*Vaccinium*. Species—*corymbosum*.

Variety denomination: The new blueberry plant claimed is of the variety denominated 'FC10-076'.

CROSS REFERENCE TO RELATED APPLICATIONS

None.

STATEMENT REGARDING FEDERALLY-SPONSORED RESEARCH AND DEVELOPMENT

None.

BACKGROUND OF THE INVENTION

The present invention relates to the discovery of a new and distinct cultivar of *Vaccinium* (*Vaccinium corymbosum*) plant, referred to as 'FC10-076', as herein described and illustrated.

The new cultivar originated in a controlled breeding program in Lowell, Oregon during Spring 2008. The objective of the breeding program was the development of superior *Vaccinium* cultivars that meet the evolving needs of the blueberry and home enthusiast industries.

The new *Vaccinium* cultivar is the result of cross-pollination. The female (seed) parent of the new cultivar is 'ZF07-114', a non-introduced, non-patented breeder seedling. The male (pollen) parent of the new cultivar is 'ZF05-032', a non-introduced, non-patented breeder seedling. The seeds resulting for the above cross were sown and small plants were obtained which were physically and biologically different from each other. Selective study during Summer 2010 in a controlled environment at Lowell, Oregon, U.S.A. resulted in the identification of a single flowering plant of the new variety.

'FC10-076' has been found to undergo asexual propagation by softwood cuttings and in vitro propagules since Summer 2010 in Lowell, Oregon. Asexual propagation techniques in Lowell, Oregon, such as softwood cuttings and in vitro cultures, have shown that the characteristics of the new variety are homogenous, stable, and strictly transmissible by such asexual propagation from one generation to another. Accordingly, the new variety undergoes asexual propagation in a true-to-type manner with all the characteristics, as herein described, firmly fixed and retained through successive generations of such asexual reproduction.

SUMMARY OF THE INVENTION

The following characteristics of the new cultivar 'FC10-076' have been repeatedly observed and are determined to be the unique characteristics of the new *Vaccinium* plant:

1) White colored inflorescences with calyx ranging from pink to blue in color,
2) Multicolored foliage including colors of green to red/pink,
3) A moderately vigorous, compact growth habit.

The new variety of the present invention can readily be distinguished from its ancestors. The parent varieties are not available for comparison. Moreover, the new variety can be readily distinguished from other similar non-parental varieties. For example, 'ZF06-079' (U.S. Plant Pat. No. 23,336) is the most similar commercially available *Vaccinium* cultivar in comparison to the new variety. Plants of the new cultivar produce a more open growth habit and smaller leaf size compared to plants of 'ZF06-079'. In addition, plants of 'ZF06-079' produce 24 seeds per berry and berries with medium firmness, whereas plants of the new cultivar have seven seeds per berry and berries with soft texture.

BRIEF DESCRIPTION OF THE DRAWINGS

The accompanying photographic illustration shows a typical specimen in full color of the new variety 'FC10-076.' The colors are as nearly true as is reasonably possible in a color representation of this type. The color values cited in the detailed botanical description accurately describe the colors of the new blueberry. The illustrated *Vaccinium* plant of the new variety was approximately one year of age and was grown in Cochranville, Pennsylvania in August 2022.

DETAILED BOTANICAL DESCRIPTION

Figure 1:
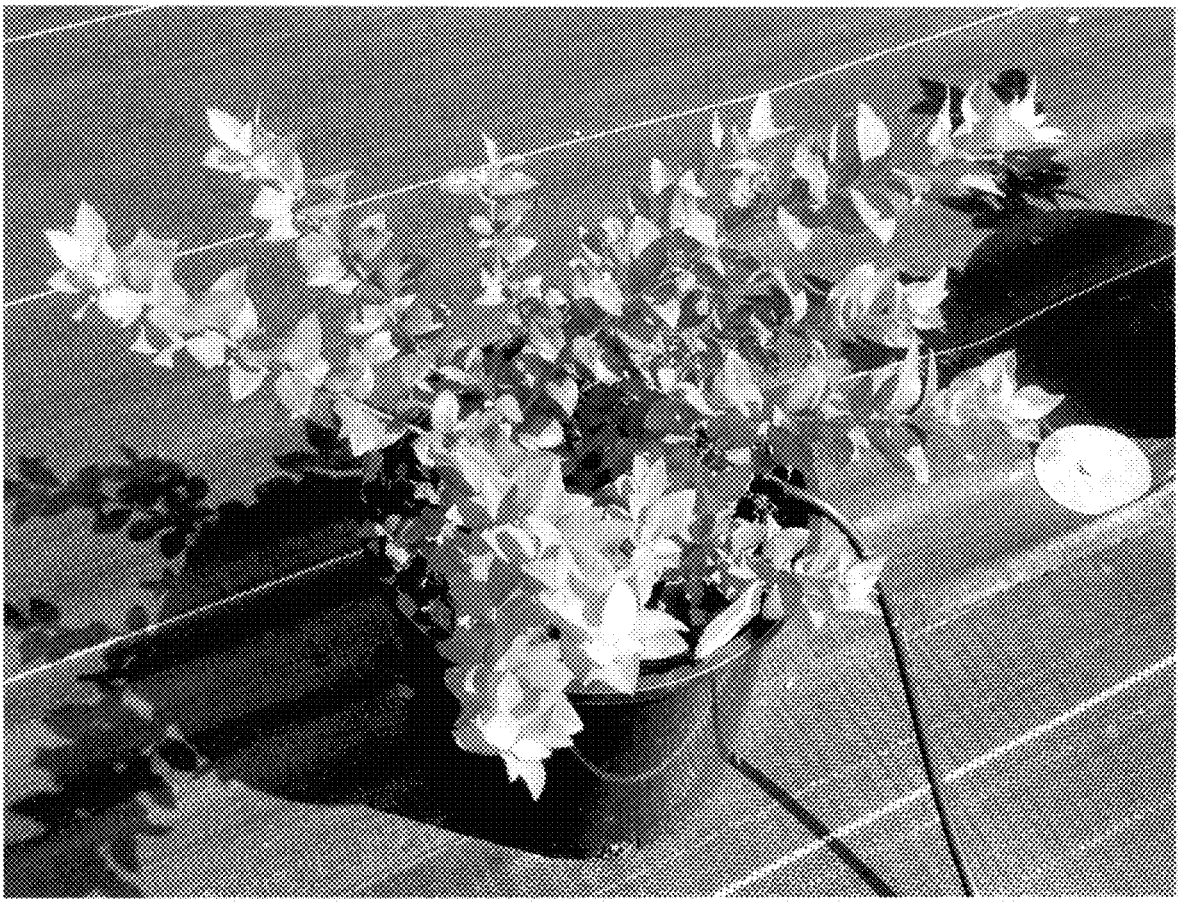
FIG. 1 illustrates container grown plant of 'FC10-076'.
Figure 2:
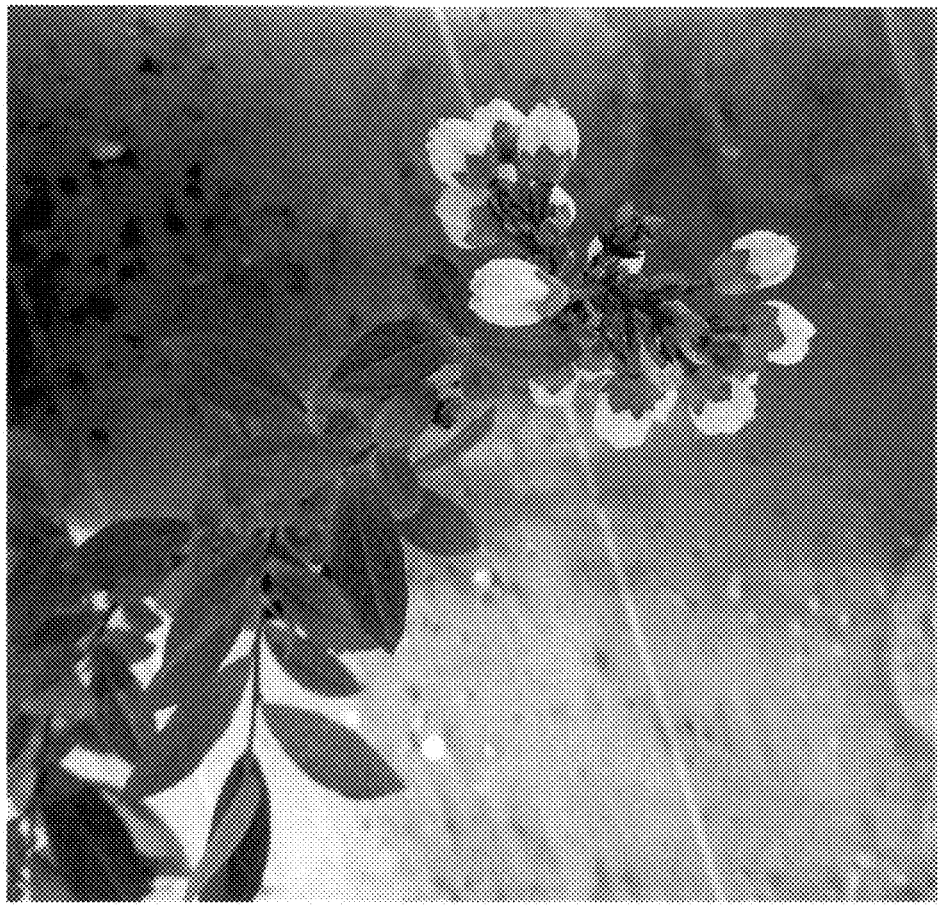
FIG. 2 illustrates a flowering branch showing calyx coloration.

The following detailed description sets forth the distinctive characteristics of 'FC10-076'. The data which defines these characteristics was collected from asexual reproductions of the original selection. Dimensions, sizes, colors, and other characteristics are approximations and averages of typical plants of two years of age set forth as accurately as possible. The chart used in the identification of colors described herein is The R.H.S. Colour Chart of The Royal Horticultural Society, London, England, 2015 edition, except where general color terms of ordinary significance are used. The R.H.S. Colour Chart designation used herein represents the closest color observed on the majority of the specified botanical feature. The color values were determined under natural light conditions in Cochranville, Pennsylvania and represent the closest color observed on the majority of the specified botanical feature.

The new blueberry plant variety 'FC10-076' has not been observed under all possible environmental conditions. The phenotype may vary somewhat with variations in environment and cultural practices such as temperature and light intensity without, however, any variance in genotype.

GENERAL

Classification:

*Family.*—Ericaceae.

*Genus.*—*Vaccinium.*

*Species.*—*corymbosum.*

Parentage:

*Female parent.*—'ZF07-114' (unpatented).

*Male parent.*—'ZF05-032' (unpatented).

Plant description:

*Commercial crop time.*—Approximately one year from a rooted cutting to finish in a one-gallon container.

*Growth habit and general appearance.*—Moderately vigorous, compact growth habit.

*Hardiness.*—USDA Zone 5.

*Size.*—Height from soil level to top of plant plane: Approximately 47.0 cm. Width: Approximately 68.0 cm.

*Branching habit.*—Freely branching. Pinching enhances branching. Quantity of lateral branches per plant: Approximately 8 main branches.

*Branch.*—Strength: Strong. Length: Approximately 30.0 cm on average. Diameter: Approximately 3.0 mm. Length of central internode: Approximately 2.0 cm. Texture: Mostly smooth with some rough areas where the wood is starting to become harder. Color of mature stems: Mostly Yellow-Green Group 146B with some coloring of Greyed-Orange Group 177B and 177A where the wood is starting to become harder.

Foliage description:

*General description.*—Fragrance: None detected. Form: Simple. Arrangement: Alternate. Time of beginning of vegetative growth: early to mid-spring.

*Leaves.*—Shape: Elliptic. Margin: Entire. Apex: Acute. Base: Cuneate. Venation pattern: Pinnate. Length of mature leaf: Approximately 3.0 cm. Width of mature leaf: Approximately 1.2 cm. Texture of upper and lower surfaces: Glabrous and glossy. Color of upper surface of young foliage: A color between Greyed-Red Group 180B and 180C with indistinguishable venation; and a color between Greyed-Purple Group 185A and 178B with indistinguishable venation. Color of under surface of young foliage: Greyed-Orange Group 174C with indistinguishable venation. Color of upper surface of mature foliage: A color between Green Group 137A and 137B with venation of Green Group 137C; and Green Group 143B, with venation of Green Group 143C. Color of lower surface of mature foliage: Green Group 137C with venation of Green Group 137D.

*Petiole.*—Length: Approximately 2.0 mm. Diameter: Approximately 1.0 mm. Texture: Glabrous. Color: Yellow-Green Group 146C.

Flowering description:

*Flowering season.*—Flowers in early spring in southeastern Pennsylvania.

*Lastingness of individual inflorescence on the plant.*—Approximately one week.

Flower description:

*General description.*—Shape: Urceolate. Quantity per plant: Approximately 180 fully open on a plant at a given time. Quantity per cluster: Approximately 6 flowers per cluster. Fragrance: Very slight, sweet. Aspect: Pendulous.

*Bud just before opening.*—Shape: Oval. Length: Approximately 8.0 mm. Diameter: Approximately 5.0 mm. Color: Green-White Group 157B.

*Corolla.*—Color: White Group 155A. Length: Approximately 1.0 cm. Width: Approximately 7.0 mm. Aperture width: Approximately 4.0 mm.

*Calyx.*—Shape: Star-shaped. Depth: Approximately 4.0 mm. Diameter: Approximately 6.0 mm.

*Sepals.*—Quantity: 7. Shape: Ovate. Margin: Entire. Apex: Acute. Base: Fused. Length: Approximately 4.0 mm. Width: Approximately 2.0 mm. Texture of upper surface: Glabrous. Texture of lower surface: Glabrous. Color of upper and lower surfaces: Primarily Green Group 143B with a little bit ranging from Greyed-Purple Group 184B, Blue-Green Group 122C, 121B, and 119B on both surfaces.

*Peduncle.*—Length: Approximately 7.0 mm. Surface texture: Unarmed and smooth. Color: Green Group 138A.

*Pedicle.*—Length: Approximately 4.0 mm. Surface texture: Unarmed and smooth. Color: Green Group 141D.

*Reproductive organs.*—Androecium: Stamen quantity per flower: Approximately 15. Stamen length: Approximately 4.0 mm. Anther shape: Narrow oblong. Anther length: Approximately 1.0 mm. Anther color: Greyed-Orange Group N167A. Pollen amount: Not observed. Gynoecium: Pistil quantity: 1 per flower. Pistil length: Approximately 8.0 mm. Stigma shape: Flat Disc. Stigma color: Yellow-Green Group 145A. Style length: Approximately 1.0 mm. Style color: Yellow-Green Group 145B. Ovary length: Approximately 2.0 mm. Ovary color: Yellow-Green Group 146C.

Fruit description:

*Date of* 50% *maturity*.—Late June to early July in Southeastern Pennsylvania.

*Fruit development period.*—80 to 85 days. Fruiting on one-year old shoots, not found on current season wood in most circumstances.

*Developing berry color.*—Red-Purple Group 75A.

*Ripe berry color.*—Greyed-Purple Group N186A.

*Berry surface wax abundance.*—Medium.

*Fruit bloom intensity*.—Strong.

*Berry flesh color.*—Greyed-Green Group 195B.

*Berry size.*—Height from calyx to scar: 1.0 cm. Diameter: 1.4 cm. Diameter of the fruit calyx basin: 1.8 mm. Depth of the fruit calyx basin: 0.7 mm.

*Berry shape.*—Semi-spherical.

*Berry firmness*.—Medium.

*Berry flavor and texture*.—Sweet flavor, soft texture.

*Suitability of mechanical harvesting*.—Not suitable.

*Uses*.—Intended for home gardens, container gardening, and/or ornamental uses.

Seed description:

*Seed abundance in fruit.*—Low, with approximately 7 seeds per berry.

*Seed color*.—Greyed-Orange Group 164A.

*Seed size.*—1.5 mm long; 1.0 mm wide.

Disease and pest resistance: Resistance to pathogens and pests common to *Vaccinium* has not been observed.

The invention claimed is:

1. A new and distinct variety of blueberry plant named 'FC10-076', substantially as illustrated and described herein.

* * * * *